United States Patent [19]
Fourneron et al.

[11] Patent Number: 6,133,463
[45] Date of Patent: Oct. 17, 2000

[54] ACTIVE PHOSPHOLIPIDS AS A VECTOR FOR ACTIVE MOLECULES

[75] Inventors: Jean-Dominique Fourneron, Marseille; Alain Fructus, Courbevoie, both of France

[73] Assignee: The Boots Company PLC., Nottingham, United Kingdom

[21] Appl. No.: 09/376,323

[22] Filed: Aug. 18, 1999

Related U.S. Application Data

[62] Division of application No. 08/773,720, Dec. 24, 1996, Pat. No. 5,985,292, which is a continuation of application No. 08/364,136, Dec. 27, 1994, abandoned.

[30] Foreign Application Priority Data

Dec. 27, 1993 [FR] France ................................ 93-15683

[51] Int. Cl.$^7$ ........................... C07F 9/02; A61K 9/127
[52] U.S. Cl. ..................... 554/79; 424/401; 424/450; 514/506
[58] Field of Search ............... 554/79; 424/450; 435/134; 514/506

[56] References Cited

U.S. PATENT DOCUMENTS

| | | | |
|---|---|---|---|
| 4,471,113 | 9/1984 | Maccoss | 536/29 |
| 4,684,632 | 8/1987 | Schulz | 514/78 |
| 4,699,778 | 10/1987 | Marty | 424/59 |
| 4,772,594 | 9/1988 | Hashimoto | 514/178 |
| 4,882,165 | 11/1989 | Hunt et al. | 424/450 |
| 5,075,340 | 12/1991 | Barua | 514/725 |
| 5,093,360 | 3/1992 | Yu | 514/463 |
| 5,194,654 | 3/1993 | Hostetler | 558/152 |
| 5,411,947 | 5/1995 | Hostetler | 514/43 |
| 5,643,600 | 7/1997 | Mathur | 424/450 |

FOREIGN PATENT DOCUMENTS

| | | |
|---|---|---|
| 0283713 | 9/1988 | European Pat. Off. . |
| 2517310 | 6/1983 | France . |
| 0036583 | 9/1981 | Germany . |
| 9116920 | 11/1991 | WIPO . |

OTHER PUBLICATIONS

Sinkula J. Pharm. Sciences vol. 64, No. 2, p. 181, Feb. 1975.
Journal of Chroatography, vol. 364, 1989, pp. 397–408 Rezanka et al.
Journal of Chromatography, vol. 364, 1989, pp. 397–408, Rezanka et al.
Agric. Biol. Chem., vol. 54(1), No. 37, pp. 191–195, 1990, Sekiya et al.
Biochemistry, vol. 29, 1990, pp. 8548–8554, Kasurinen et al.
Journal of Lipid Research, vol. 33, No. 6, 1992, pp. 879–887, Parks et al.
63–Pharmaceuticals, vol. 116, 1992, p. 317, Hibino et al.
Chemical Abstracts, vol. 113, 1990, p. 48, Hibino et al.
13–Mammalian Biochem, vol. 113, 1990, p. 459, Tokumura et al.
Method of Enzymology, vol. 72, Lipids, Part D, 1981, pp. 632–639, [53], Eibl et al.
Arneim–Forsch., Drug res., vol. 35(l), Nr. 3, 1985, pp. 587–592, Tokumura et al.
Biochemistry, vol. 14, No. 23, 1975, pp. 5021–5033, Chakrabarti et al.
Pharmazie, vol. 39, 1984, H. No. 3, pp. 150–153, Kertscher et al.
Chemistry and Physicis of Lipids, vol. 50, No. 2, 1989, pp. 135–142, Sale et al.

*Primary Examiner*—Gollamudi S. Kishore
*Attorney, Agent, or Firm*—Arent Fox Kintner Plotkin Kahn

[57] ABSTRACT

An active phospholipid of the formula

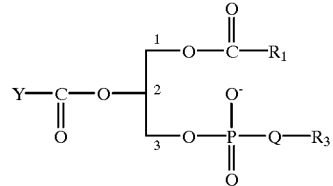

wherein $R_1$ is aliphatic of 14 to 24 carbon atoms saturated or containing 1 or 2 unsaturations, $R_3$ is a residue selected from the group consisting of choline, ethanolamine, glycerol, serine, inositol, ethanol, n-propanol, n-butanol and ethylene glycol and

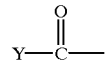

is an active group in the 2-position of the glycerol released by phospholipases and cosmetic and dermatological compositions containing the same useful for treating or caring for the skin.

10 Claims, No Drawings

ACTIVE PHOSPHOLIPIDS AS A VECTOR FOR ACTIVE MOLECULES

This is a divisional of application Ser. No. 08/773,720 filed on Dec. 24, 1996, now U.S. Pat. No. 5,985,292, which is a continuation of application Ser. No. 08/364,136 filed Dec. 27, 1994, now abandoned.

STATE OF THE ART

Phospholipids are very widely found in nature as they are the major constituents of the walls of animal and vegetable cells. Their fundamental property is that of being able to form "double layers", constituting the structure of the cells walls. The constitution of natural phospholipids is very varied, this variety playing important roles in cellular metabolisms, roles which are sometimes still unclear.

The structure of phospholipids is the following:

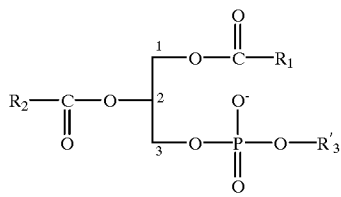

The natural glycerophospholipids contain four ester functions: the carboxylic ester functions

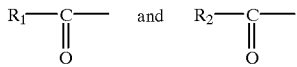

respectively in position 1 and 2 of the glycerol on the one hand and between the phosphorus and the variable "polar head", on the other hand, which is constituted by $R_3$—O—$PO_2$—O—. $R_1$ and $R_2$ are individually an aliphatic chain of 14 to 24 carbon atoms, saturated with 1 or 2 unsaturations such as palmitic acid, oleic acid, linoleic acid, stearic acid, or myristic acid and $R'_3$ is a remainder of choline, ethanolamine, glycerol, serine or inositol.

Thus, two fatty acids are esterified at positions 1 and 2 of the glycerol and the 3rd hydroxyl of the glycerol is esterified by a phosphatidyl ester. Position 2 of the glycerophospholipid is particularly important. In fact, many phospholipase A2's exist in tissues, particularly in the skin, so as to release the corresponding fatty acid,

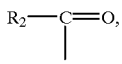

which can then be metabolized in the organism. These phospholipase A2's are notably described in Slotta, (1960), The Enzyme, Vol. 4, p. 552 and Van Deenen et al., (1966), Ann. Rev. Biochem., Vol. 35 (1), p. 674. Furthermore, the exogenous phospholipids have an affinity for tissues and particularly for the skin, and are capable of being absorbed into the cell walls.

OBJECTS OF THE INVENTION

It is an object of the invention to provide novel phospholipids of formula I and a process for their preparations.

It is another object of the invention to provide novel cosmetic and dermatological compositions and a novel method of caring for the skin of warm-blooded animals including humans.

These and other objects and advantages of the invention will become obvious from the following detailed description.

THE INVENTION

The novel phospholipids of the invention have the formula

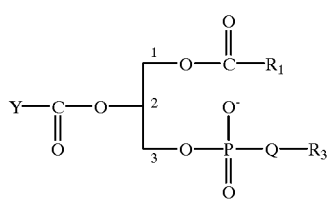

wherein $R_1$ is aliphatic of 14 to 24 carbon atoms saturated or containing 1 or 2 unsaturations, $R_3$ is a residue selected from the group consisting of choline, ethanolamine, glycerol, serine, inositol, ethanol, n-propanol, n-butanol and ethylene glycol and

is an active group in the 2-position of the glycerol released by phospholipases.

The cells are provided with functional elements by means of semi-synthetic phospholipids; by incorporating functional molecules in position 2 of a phospholipid. They are rendered particularly bio-available because they will rapidly penetrate the tissues and then the cells due to the affinity of their phospholipid residues with the phospholipids of the membranes and will then release the functional molecule under the action of the phospholipase A2's.

Examples of an aliphatic of 14 to 24 carbon saturated or containing 1 to 2 unsaturations are those derived from oleic acid, palmitic acid, linoleic acid, stearic acid and myristic acid. Examples of $R_3$ are ethyl, propyl or butyl, preferably ethyl.

The preferred phospholipids of the invention are those of formula I wherein the active molecule to be grafted at position 2 is chosen from the following molecules; vitamin A acid, all-trans retinoic acid, 9-cis retinoic acid, 13-cis retinoic acid, essential fatty acids such as γ-linolenic acid, α-linolenic acid, eicosapentaenoic acid (EPA), docosahexaenoic acid (DHA), α-hydroxylated acids such as glycolic acid, lactic acid, tartaric acid, α-methyllactic acid, α-hydroxybutyric acid, gluconic acid, mandelic acid, mucic acid, malic acid, α-phenyllactic acid, saccharic acid, tartronic acid; the various acids such as kojic acid, asiatic acid, madecassic acid, benzoic acid, glutamic acid, malonic acid, phytic acid, ascorbic acid, nordihydroguaiaretic acid, salicylic acid, 18β-glycyrrhetinic acid; amino acids such as tyrosine, hydroxyproline, lysine, arginine, the small functional peptides such as pyroGlu-Glu-Asp-Ser-GlyOH or Gly-His-Lys or Arg-Gly-Asp-Ser, or diacid moesters such as farnesil succinate, retinol succinate and diacid monoamides of the formula

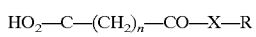

in which n is an integer of 2 to 16, X is sulfur, nitrogen or oxygen and R is included in the above list of acids.

A more particular subject of the present invention is active phospholipids as defined above wherein the active molecule to be grafted at position 2 is chosen from the following molecules: vitamin A acid, γ-linolenic acid, eicosapentaenoic acid (EPA), docosahexaenoic acid (DHA), kojic acid, asiatic acid, madecassic acid, glutamic acid, phytic acid, glycolic acid, lactic acid, ascorbic acid, nordihydroguaiaretic acid, amino acids such as tyrosine, small functional peptides such as pyroGlu-Glu-Asp-Ser-GlyOh or Gly-His-Lys or Arg-Gly-Asp-Ser and 18β-glycyrrhetinic acid.

The novel process of the invention for the preparation of phospholipids of formula I comprises subjecting a phospholipid or mixtures thereof from natural sources of the formula

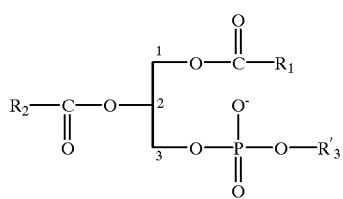

II which $R_1$ and $R_2$ are individually aliphatic of 14 to 24 carbon atoms saturated or having 1 or 2 unsaturations and $R_3$ is the remainder of a member of the group consisting of choline, ethanolamine, glycerol, serine and inositol to a substitution reaction to replace $R'_3$ with a member of the group consisting of ethyl, propyl and butyl by enzymatic trans phosphatidylation to obtain a product of the formula

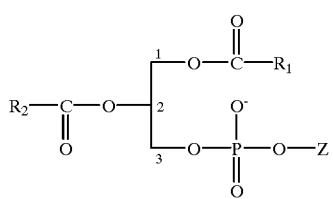

III wherein $R_1$ and $R_2$ have the above definitions and Z is selected from the group consisting of ethyl, propyl and butyl, subjecting the latter to enzymatic hydrolysis of the 2-ester group to obtain a compound of the formula

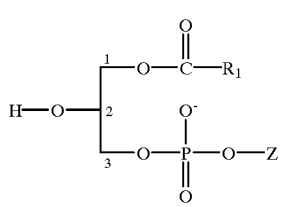

IV wherein $R_1$ and Z have the above definition and reacting the latter with an acid anhydride of the formula

V or a corresponding mixed anhydride in which

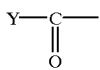

is a remainder of an active molecule as defined above, to obtain a compound of formula I.

The staring materials are natural phospholipids, particularly those extracted from egg yolk using commercially available or industrially prepared egg yolk or from soya or soya lecithin.

Generally, the chemistry of the glycerophospholipids is a chemistry carried out in mixtures of solvents to accommodate the amphipatic nature of these molecules. The products are obtained very dilute and therefore, the costs are high. As a result, practically no use of these products as perfectly defined molecules exists. The preparation process for the active phospholipids, consists, starting with natural phospholipids, of acting successively on two of the ester bonds of the glycerophospholipids by replacing the polar head $R_3$—O— and then by selective enzymatic hydrolysis of position 2.

The product of formula I wherein Z is ethyl, propyl or butyl can be optionally converted by known means to compounds of formula I wherein Z has the definition of $R_3$.

In a preferred mode of the process, the natural sources of phospholipid are of animal or vegetable origin such as egg yolk and vegetable lecithin such as soya, preferably phosphatidyl choline or phosphatidylethanolamine or mixtures thereof.

Phosphatidylcholine and phosphatidylethanolamine correspond to a product of formula II in which —O—$R'_3$ is a remainder of choline

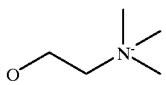

and a remainder of ethanolamine

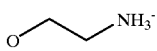

Preferably, the substitution of $R'_3$ with ethyl or propyl or butyl is effected by enzymatic transphosphatidylation using phospholipase D in ethanol, propanol or butanol (Enzyme Handbook, Barman, p. 545) which reaction is complete and univocal. The enzymatic hydrolysis to obtain the ethyl, propyl or butyl lysophosphatidyl of formula IV is effected with unpurified phospholipase $A_2$ in a $Ca^{++}$ ion calcium medium.

The acylation of the hydroxy of formula IV with a biologically active molecule or molecules to be transported into the membranes is effected by acidification of the ethanol, propanol or butanol lysophosphatidyl followed by reaction with an acid anhydride or mixed acid anhydride in an organic solvent such as diethyl ether or toluene.

The originality of this synthesis resides in the close implication between traditional chemical stages and the use of the specificity of several lipolytic enzymes. The principal innovation resides in the use of the intermediate ethanol, propanol or butanol phospholipid (PZ) which intervenes to facilitate all the stages of the synthesis. The good enzymatic activities of the phospholipase A2 and of the pancreatic lipase on the phospholipids of this type allow the use of crude enzymes originating from the same source: pancreatic powder.

The ethanol, propanol or butanol phospholipid is obtained in a univocal manner and the method of purification by precipitation which is used allows a pure product in the form of a calcium salt to be obtained. The interest of this protocol relative to those described (Eibl et al., 1981, and Cestaro, et al., 1989) is the obtaining of a calcium salt from the (PZ) which can be easily isolated to the exclusion of the sodium salt which is formed in the presence of sodium acetate, and the absence of parasitic products such as phosphatidic acid or non-converted starting products. Furthermore, the use of the calcium salt in the following stage which makes use of a hydrolysis catalyzed by strictly calcium-dependent phospholipase A2 (PA$_2$) is far more favorable than the use of phosphatidylethanol in acid form.

A more particular subject of the present invention is a process for active phospholipids as defined above, characterized in that the active substance to be incorporated in the phospholipid in position 2 is selected from the group consisting of vitamin A acid, all-trans retinoic acid, 9-cis retinoic acid, 13-cis retinoic acid, essential fatty acids such as γ-linolenic acid, α-linolenic acid, eicosapentaenoic acid (EPA), docosahexaenoic acid (DHA), α-hydroxylated acids such as glycolic acid, lactic acid, tartaric acid, α-methyllactic acid, α-hydroxybutyric acid, gluconic acid, mandelic acid, mucic acid, malic acid, α-phenyllactic acid, saccharic acid, tartronic acid; the various acids such as kojic acid, asiatic acid, madecassic acid, benzoic acid, glutamic acid, malonic acid, phytic acid, ascorbic acid, nordihydroguaiaretic acid, salicylic acid, 18β-glycyrrhetinic acid; amino acids such as tyrosine, hydroxyproline, lysine, arginine, small functional peptides such as pyroGlu-Glu-Asp-Ser-GlyOH or Gly-His-Lys or Arg-Gly-Asp-Ser or also diacid monoesters such as farnesil succinate, retinol succinate and diacid monoamides of general formula

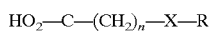
HO$_2$—C—(CH$_2$)$_n$—X—R in which n is an integer between 2 and 16, X is sulfur, nitrogen or oxygen atom and R is a group included in the above list of acids, and quite particularly from the following substances: vitamin A acid, γ-linolenic acid, eicosapentaenoic acid (EPA), docosahexaenoic acid (DHA), kojic acid, asiatic acid, madecassic acid, glutamic acid, phytic acid, glycolic acid, lactic acid, ascorbic acid, nordihydroguaiaretic acid, amino acids such as tyrosine, small functional peptides such as pyroGlu-Glu-Asp-Ser-GlyOh or Gly-His-Lys or Arg-Gly-Asp-Ser and 18β-glycyrrhetinic acid.

Among the products of formula I are the following active phospholipids which can be vectors for the active substances as defined above intended for particular uses. An active phospholipid as a vector for a retinol ester such as vitamin A acid or one of its isomers such as all-trans retinoic acid, 9-cis retinoic acid or 13-cis retinoic acid, can be used to obtain an anti-acne activity, particularly an activity on comedones or an anti-wrinkle activity.

An active phospholipid as a vector for γ-linolenic acid is used for the restoration of the fluidity of membrane walls and for the improvement of the condition of the skin of atopic people for whom a lack of γ-linolenic acid causes significant disturbances at the level of the skin. An active phospholipid as a vector for eicosapentaenoic acid (EPA) and/or docosahexenoic acid (DHA) is used for the treatment of psoriasis because it has been shown that an exogenous supply of fatty acids greatly improves the condition of skin suffering from psoriasis.

An active phospholipid as a vector for an α-hydroxy acid such as glycolic acid, lactic acid, tartaric acid, α-methyl lactic acid, gluconic acid, mandelic acid, mucic acid or malic acid is used for the treatment of hyper-keratoses, acne, aging, particularly actinic aging. The asiatic and madecassic acids, extracted from the Centella Asiatica plant are known to have healing and anti-cellulite properties. They cause the fibroblasts to produce collagen of excellent quality. Grafted and transported by an active phospholipid, their activity is greatly increased.

Phytic acid is an excellent chelating agent of metals. Therefore, it possesses anti-oxidizing, anti-radical and anti-metallo-enzyme properties, particularly anti-protease properties. Phytic acid can be incorporated in position 2 of an active phospholipid and thus make it more bio-available. Ascorbic acid or vitamin C is also an excellent anti-radical and anti-oxidizing agent. It participates in all sorts of biochemical cycles, particularly in the skin. Incorporated with an active phospho-lipid, it is far more stable and more bio-available, very useful for example in the case of exposure to solar radiation, where it traps biologic iron and limits the harmful effects of inflammation.

Nordihydroguaiaretic acid is also an excellent anti-oxidizing agent and it is used for the treatment of sun keratoses. Grafted in position 2 of an active phospholipid, its bioavailability is considerably increased which allows lower doses to be used for the same activity and therefore the harmful side effects to be reduced. An active phospholipid carrying tyrosine in position 2 is easily absorbed by the skin and allows a deeper suntan to be obtained because the synthesis of melanine is based on the use of tyrosine. 18β-glycyrrhetinic acid is a very good anti-inflammatory but not very soluble and it has difficulty in penetrating into the skin. Grafted in position 2 of an active phospholipid, its penetration into the skin is greatly enhanced and so is its effectiveness.

The novel cosmetic or dermatological compositions of the invention for the treatment and care of skin of warm-blooded animals, including humans are comprised of an effective amount of a phospholipid of formula I and a skin care excipient. The compositions are useful for the treatment of skin suffering from acne, dehydration, wrinkles and damaged skin. The compositions preferably contain 0.1 to 10%, more preferably 0.4 to 5%, by weight of the total composition of phospholipid.

Suitable excipients are used to supply these various active phospholipids to the skin. Among the excipients, surfactants are frequently used such as sorbitan esters like sorbitan stearate, oxy-ethylenated sorbitan esters like POE sorbitan palmitate, sucrose esters like sucrose cocoate, glucose esters or methylglucose esters oxyethylenated or not, like methylgluceth-20 or methylglucose sesquistearate, neutralized acyl phosphates like potassium cetylphosphate, ethoxylated fatty acids like ethoxylated stearic acid, ethoxylated fatty alcohols like ethoxylated stearylic alcohol, more or less de-oiled lecithins from egg or soya, hydrogenated or not and ethoxylated vegetable sterols.

The excipients can also contain wetting agents, preservatives such as methylparaben, biosol, bronopol, perfumes, coloring agents, fillers such as talc or polymethacrylate. Optionally, the compositions according to the invention can also contain insoluble or soluble additives such as liposoluble or hydrosoluble complementary active ingredients, for example sun filters or solar radiation screens, to give them a protective power against solar radiation, vitamin extracts and anti-oxidizing agents and dispersing agents and stabilizers.

When the additives are insoluble in the oil and aqueous phases, they therefore constitute a supplementary phase.

They are chosen for example from the following products: perfluoroethers such as FOMBLIN (R) from the MONTE-CATINI Company, insoluble pigments such as: titanium oxides, rutile titanium oxide, anatase titanium oxide, pyrogenated titanium oxide such as P 25 (R) from Degussa, micronized titanium oxide such as SUN VEIL (R) from Ikeda, titanium oxide treated superficially with silicones or with amino acids, or with lecithin, or with metallic stearates, iron oxide, iron oxide treated superficially with silicones, or with amino acids, or with lecithin, or with metallic stearates, zinc oxide, micronized zinc oxide such as UFZO (R) from Cosmo Trends Corporation and mica covered with titanium oxide.

Also the dermatological or cosmetic compositions may contain one or more complementary liposoluble active ingredients incorporated in the oily phase of the emulsion, chosen in particular from the following substances for which the preferred percentages are indicated below, expressed relative to the final complete formula:

Vitamin A palmitate: 500 to 10,000 IU/g.

Liposoluble sun filters: octyl methoxycinnamate: 0.5 to 10%, isoamyl ethoxycinnamate: 0.5 to 10%, octyl dimethyl 25 paba: 0.5 to 8%, octyl salicylate: 0.5 to 5%, butyl methoxydibenzoyl methane: 0.5 to 5%, benzophenone 3: 0.5 to 10%, octyl triazone: 0.5 to 5%, ethyl 4-polyethoxy aminobenzoate: 0.5 to 10%, isopropyl 4-dibenzoyl methane: 0.5 to 5%.

Nonsaponifiable matter from corn, karite, soya or avocado: 0.1 to 3%.

Ximenoil (R) (oily mixture containing 50% Ximenic acid): 0.1 to 5%, essential extract of sesame oil: 0.1 to 4%, peroxidized corn oil: 0.1 to 10%, tocopherol acetates: 0.05 to 7%, natural tocopherols: 0.05 to 5%, farnesol: 0.05 to 5%, linoleic acid 2 to 10%.

Also the dermatological or cosmetic compositions may contain one or more hydrosoluble complementary active ingredients incorporated in the aqueous phase of the emulsion, chosen notably from sodium lactate, extracts of Hafnia biolyzate, extracts of *Klebsellia pneumoniae* biolyzate and hydrosoluble sun filters.

The hydrosoluble complementary active ingredients can also be chosen from the above substances for which the preferred percentages are indicated, expressed relative to the final complete formula:

neutralized 2-phenyl benzimidazol 5-sulfonic acid: 0.5 to 8% neutralized 2-hydroxy 4-methoxybenzophenone 5-sulfonic acid: 0.5 to 5%

Ascorbic acid: 0.5 to 10%, caffeine benzoate: 0.1 to 5%, phytic acid: 0.1 to 5%, mucic acid: 0.1 to 5%, hydrolysates of vegetable proteins: 0.1 to 10%, polyglucan: 0.1 to 5%

Mexican mimosa extract: 0.5 to 20%, chitosan: 0.5 to 20%, marine animal serum: 0.1 to 3%

Hirudin extract: 0.5 to 10%, meristem extract: 0.1 to 5%, procyanodolic oligomers: 0.05 to 3%, yeast extracts: 0.05 to 3%, panthenol: 0.05 to 5%, centella asiatica extract: 0.05 to 3%, glycyrrhetinic acid: 0.05 to 2%.

The cosmetic compositions of the invention can be presented in all the forms used in cosmetology: creams or gels in pots or in tubes, milks in glass or plastic bottles and optionally in dosing-bottles or phials.

The dermatological compositions as defined above can be presented in the form of liquid or solid preparations for topical use and particularly in one of the following forms:

fatty gels, simple, water-in-oil emulsions, simple, oil-in-water emulsions, multiple emulsions, for example a triple water-in-oil-in-water or oil-in-water-in-oil emulsion, complex emulsions containing liquid crystals forming lipidic double layers surrounding the oil phases, an oil-in-water emulsion containing liquid crystals, oil-in-water or water-in-oil micro-emulsions, emulsions containing dispersed oily phases, which are different from and insoluble with each other, pseudo-emulsions or dispersion of an oily phase in an aqueous phase and stabilized with gelatinizing agents such as Lubragel (R), (polyglyceryl methacrylate marketed by SEDERMA, FRANCE), Pemulen (R), Hypan (R), Xanthan gum, CMC, hydroxyethyl cellulose, Amigel (R), Polyvinylpyrrolidone, Amercell HM1500 (R), or a mixture of two or more of these gelatinizing agents, without traditional surfactants.

The method of treating comedones comprises applying to comedones an effective amount of a phospholipid of formula I containing a vector for a retinal ester such as vitamin A acid or one of its isomers such as all-trans retinoic acid, 9-cis retinoic acid.

The method can also be used to treat dry or dehydrated skin or to supply the skin with living organisms and active substances.

In the following examples, there are described several preferred embodiments to illustrate the invention. However, it is to be understood that the invention is not intended to be limited to the specific embodiments.

EXAMPLE 1

The Preparation of a Phospholipid as a Vector for Vitamin A Acid

The conversion of a mixture of phpholipids extracted from a natural source into a vector compound for vitamin A acid is carried out by a three-stage process:

1) Extraction of the natural phospholipids and their conversion into a single compound,
2) Selective hydrolysis in position 2,
3) Reacylation of the lyso-phospholipid.

The following abbreviations will be used:

PC: phosphatidylcholine:

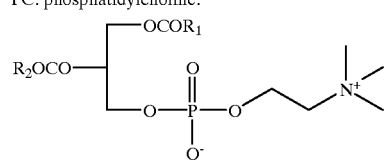

PE: phosphatidylethanolamine:

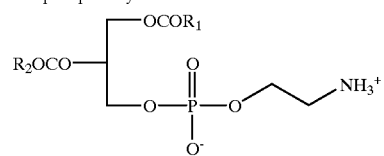

-continued

PET: phosphatidylethanol:

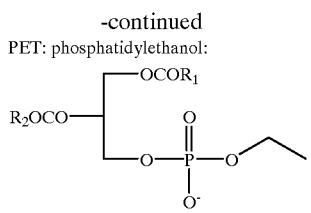

in which $R_1$ and $R_2$ have the above definitions.

1) Extraction of the natural phospholipids and their conversion into a single compound.

a) Extraction of the natural phospholipids

The phospholipid source used was chicken egg yolk with commercially-available eggs or industrially-prepared egg yolk being used. Starting with commercially-available eggs, the first stage was their hardening achieved at about 100° C. over about 10 minutes. The yolks were then collected and extraction was carried out either directly or after drying. The extraction was carried out first with 3 extractions with 200 ml of acetone for 400 g of wet yolk by simple stirring of the crushed yolk in the solvent. The suspension was filtered and the solid was treated again with acetone. The creamy-white residual solid was dried and dispersed 3 times in 200 ml of ethanol. After filtration, the ethanolic phase was either preserved in the volume necessary for the following stage, or evaporated under reduced pressure. The residue was diluted in a minimum of dichloromethane (DCM) and 500 ml of acetone were added. The phospholipids precipitated and the suspension was kept at 4° C. for 16 hours, then filtered and dried.

The extraction rate was on average 1 g to phospholipids per egg yolk and 150 g per kilo of dry product were obtained. The mixture was constituted for the main part by PC and PE in the proportions of 4 to 1.

b) Conversion of the PC/PE mixture into PET

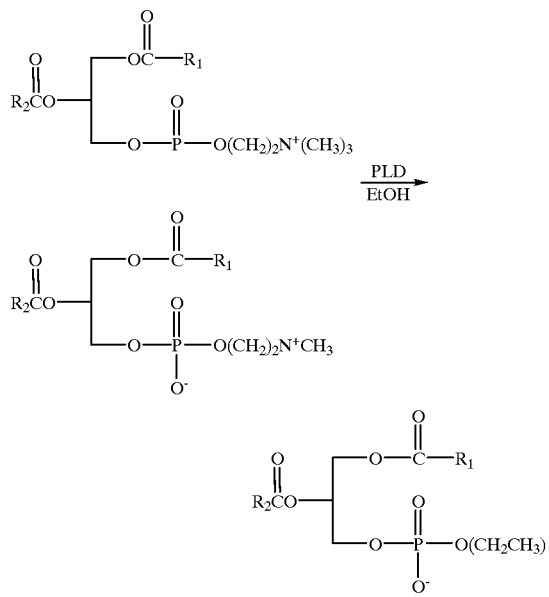

in which $R_1$ and $R_2$ have the above meanings.

This conversion was carried out using the property of phospholipase D (PLD) to catalyze the transphophatidylation reactions which enable the polar head of the phospholipids to the modified. The PLD was extracted from cabbage leaves by chopping 1 kg of white leaves using a "blender" with 1 liter of distilled water. The ground-up product was filtered and the filtrate of 1.1 to 1.2 liters was used as is or diluted. 40 mM of calcium chloride were added and the pH was between 5 and 6.

A half volume of an ethanolic solution of the PC/PE mixture in a variable quantity of 10 to 80 g/l, preferably 40 g/l, was added to one volume of enzymatic extract with vigorous stirring. The development of the reaction was monitored by thin layer chromatography (TLC). After a time varying from 2 to 10 hours, the disappearance of the PC and the PE and the formation of a gummy precipitate were observed. The aqueous phase was eliminated and the precipitate was dissolved in the minimum of dichloromethane or other appropriate solvent, filtered, then purified by precipitation in 400 ml of acetone with stirring. Filtration and drying were carried out to obtain a creamy white product in a yield of 60 to 90%, which was the calcium salt of phosphatidylethanol.

2) Hydrolysis in position 2 of the PET to obtain the lyso-PET

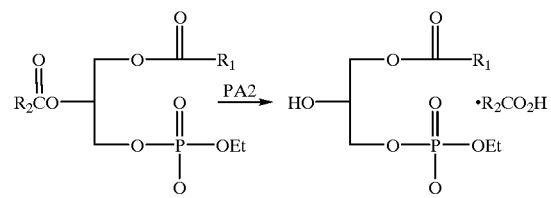

in which $R_1$ and $R_2$ have the above meanings.

The source of PA2 used was porcine pancreatic powder (Fluka) and 2 g of enzymatic powder were dissolved in 10 to 20 ml of a solution of 50 mM of boric acid and 50 mM of calcium chloride. The pH was adjusted to 2 to 3 over 20 minutes and then the pH was returned to 7 to 8 with 1N sodium hydroxide. A solution of 10 g of PET was then added in the form of 16 mmol of the calcium salt in 100 to 200 ml of ether and the mixture was vigorously stirred. The development of the reaction was monitored by thin layer chromatography and a regular disappearance of the PET in favor of the lyso-PET and fatty acids released by the hydrolysis was observed. As the end of the reaction, filtration was carried out on celite. To purify the lyso-PET by precipitation, the ether was evaporated so that only a sufficient volume for the solubility of the solution remained and the solution was poured into 400 ml of acetone with vigorous stirring. The lyso-PET in the form of the calcium salt, creamy white in color, precipitated while the released fatty acids were soluble in the acetone. Filtration and drying were carried out to obtain the lyso-PET derivative in a yield of 60 to 90%.

3) Reacylation of position 2.

This stage was divided into two sub-stages: acidification of the lyso-PET and actual acylation after optionally obtaining in situ an anhydride of vitamin A acid.

A) acidification of the lyso-PET.

The lyso-Pet previously obtained contained salt forms and the acid form was obtained by dissolution of 5 g of the product in 10 ml of chloroform or dichloromethane and 12 ml of methanol mixture and washing 3 times with 10 ml of 1N hydrochloric acid. The organic phase was washed with distilled water and evaporated under reduced pressure in the presence of toluene. The crude product was dried under reduced pressure in a dessicator.

B) Actual acylation after optionally obtaining in situ an anhydride of vitamin A acid.

The acylation of the acid form of the lyso-PET was carried out using the acid that it is desired to introduce in activated form. For high value acids such as retinoic acid or polyunsaturated acids, a mixed anhydride with pivalic acid or dicyclohexylcarbodiimide (DCC) in the reaction medium was prepared. In the case where a mixed anhydride was prepared, it was the acyl of the mixed anhydride which was at least sterically hindered which transferred onto the receiving alcohol.

Acylation by the anhydride

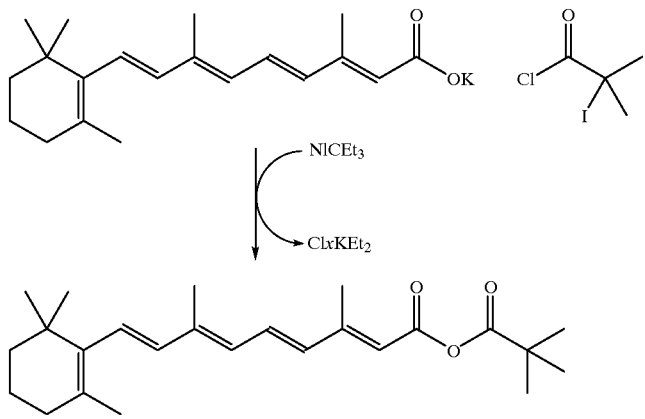

Preparation of the anhydride: 0.2 ml (1.6 mmol) of pivaloyl chloride were added to a solution of 500 mg of vitamin A acid (1.66 mmol) in 20 ml of toluene and ethyl ether containing 1 ml of triethylamine (7.2 mmol). The reaction was carried out shaded from the light and under an inert atmosphere. Monitoring by TLC indicated the disappearance of the acid in a few minutes.

Acylation in which $R_1$ has the meaning indicated above.

Next, 600 mg (1.3 mmol) of the lyso-PET dissolved in 10 ml of toluene and ethyl ether and 12 mg of 4-dimethylamino-pyridine (0.13 mmol) and 1 ml of toluene or ethyl ether were added. The development of the reaction was monitored by TLC and the reaction was complete (disappearance of the lyso-PET) after 6 to 10 hours. Filtration was carried out on celite and 10 ml of 1N hydrochloric acid were added. The organic phase was washed with water and evaporation was carried out in the presence of toluene. The crude mixture was fractionated by chromatography on silica and the yield after purification was 60% to obtain 600 mg of PET-vitamin A.

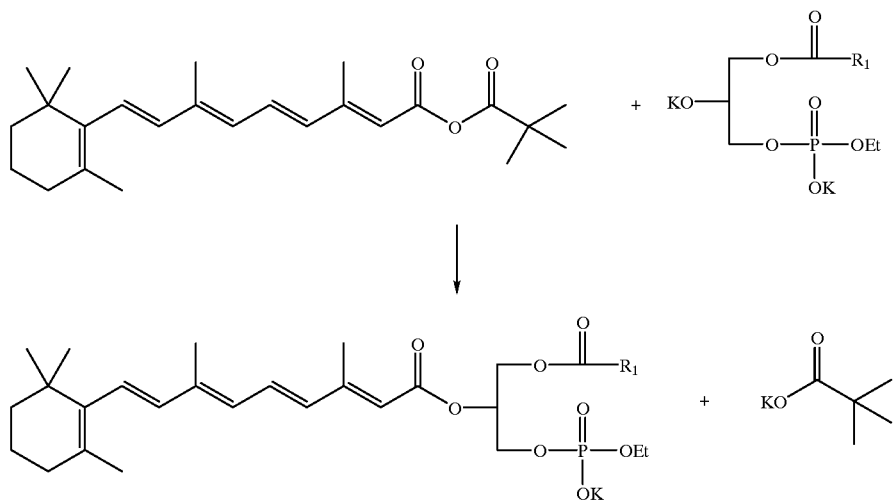

Acylation with dicyclohexylcarbodiimide (DCC)

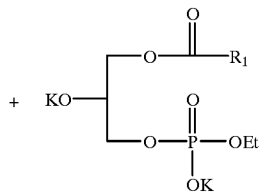

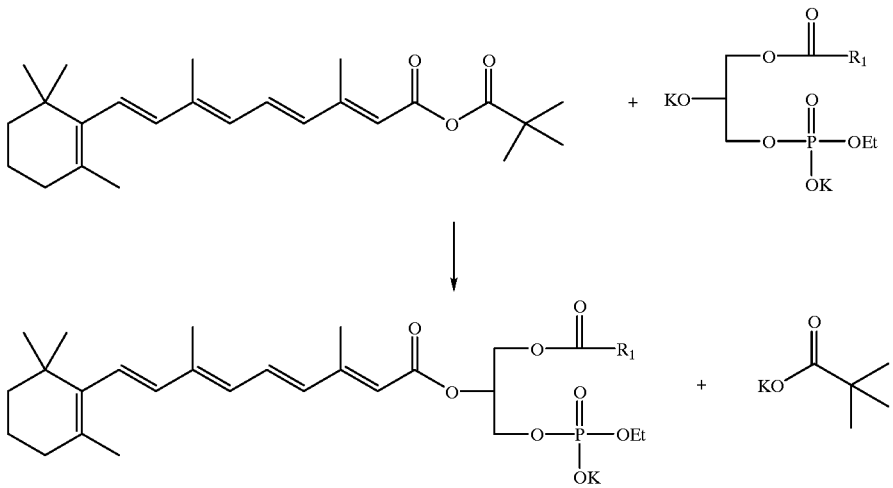

600 mg (1.3 mmol) of lyso-PET were dissolved in 10 ml of toluene and ethyl ether and 12 mg of (0.13 mmol) in 1 ml of toluene or ethyl ether and 322 g (1.56 mmol) of dicyclohexylcarbodiimide were added to a solution of 500 mg (1.66 mmol) of vitamin A acid in 20 ml of toluene or ethyl ether containing 1 ml of triethylamine (7.2 mmol). The development of the reaction was monitored by TLC and the reaction was complete (disappearance of the lyso-PET) in 6 to 10 hours. Filtration was carried out on celite and 10 ml of 1N hydrochloric acid were added. The organic phase was washed with water and evaporation was carried out n the presence of toluene. The crude mixture was fractionated by chromatography on silica to obtain a yield after purification of 60% or 600 mg of PET-vitamin A.

EXAMPLE 2 the following oily phase was heated to 70° C.:

| | |
|---|---|
| Stearamidopropyl PG-dimonium chloride Phosphate (CTFA name) | 3.0 g |
| Cocamidopropyl PG-dimonium chloride Phosphate (CTFA name) | 1.0 g |
| Cetyl alcohol | 3.0 g |
| Myristyl myristate | 5.0 g |
| Hydrogenated polyisobutene | 2.0 g |
| Karité butter | 2.0 g |
| Propylene glycol stearate | 3.0 g |
| Silicone oil | 2.0 g |
| Vegetable oil | 5.0 g |
| Anti-oxidant | 0.2 g |
| Oleyl acetate | 1.0 g |

Furthermore, the following aqueous phase was prepared and was heated to 70° C.:

| | |
|---|---|
| Demineralized water SQF | 100.0 g |
| Glycerin | 10.0 g |
| Modified hydroxy ethylcellulose | 0.5 g |
| PVP | 1.0 g |
| Preservatives | 0.52 g |

The oil-in-water (O/W) emulsion was prepared by vigorously mixing the two phases at 90° C. for 10 minutes, followed by slowly cooling under moderate stirring. 0.5% of perfume, then 0.5% of all-trans 2-Retinoyl Phosphatidyl Ethanol were added at 45° C. The mixture was cooled to 25° C. and this cationic O/W emulsion was used in the treatment of acne.

EXAMPLE 3

Cream for the treatment of atopic skins

| | |
|---|---|
| γ linolenyl Phosphatidyl Ethanol | 5.0 g |
| Potassium alkyl phosphate | 2.0 g |
| Ethyl hexyl palmitate | 8.0 g |
| Hydrogenated lanolin | 5.0 g |
| Triglycerides of fatty acids | 4.0 g |
| Sorbitan stearate | 1.0 g |
| Neutralized carboxyvinyl polymer | 0.4 g |
| Preservatives | 0.4 g |
| Purified water SQF | 100.0 g |

EXAMPLE 4

Cream for the treatment of psoriasis

| | |
|---|---|
| 2-EPA phosphatidyl Ethanol | 1.0 g |
| 2-DHA phosphatidyl Ethanol | 1.0 g |
| Cylcerol stearate | 4.0 g |
| Sorbitan palmitate | 6.0 g |
| Perhydrosqualene | 5.0 g |
| Diisopropyl-cyclohexane | 7.0 g |
| Capric/caprylic triglycerides | 9.0 g |
| Glycerin | 5.0 g |
| Preservatives | 0.35 g |
| Purified water SQF | 0.35 g |

EXAMPLE 5

Sun Lotion

| | |
|---|---|
| 2-Ascorbyl Phosphatidyl ethanol | 3.0 g |
| Sun filters | 5.0 g |

-continued

| | |
|---|---|
| Vaseline oil | 10.0 g |
| Cetearyl octanoate | 4.0 g |
| De-oiled soya phospholipids | 5.0 g |
| Silicone oil | 2.5 g |
| Cetyl ether P.O.E. | 2.0 g |
| Sorbitan stearate | 1.0 g |
| Preservatives | 0.35 g |
| Aromatic composition | 0.5 g |
| Purified water SQF | 100.0 g |

EXAMPLE 6

Multiple emulsion for the treatment of actinic aging.

The following aqueous phase, called the internal aqueous phase, was heated to 80° C.:

| | |
|---|---|
| Demineralized water | 26.52 g |
| Methylparaben | 0.1 g |
| Magnesium sulfate | 0.28 g |
| Glycerin 30' B | 0.8 g |
| O-cymen-5-ol | 0.04 g |

The following oily phase was heated separately:

| | |
|---|---|
| Glyceryl isostearate | 2.0 g |
| Polyoxyethylenated hydrogenated ricin oil (7 mols) | 0.2 g |
| Soya oil | 8.2 g |
| Propylparaben | 0.06 g |
| Volatile silicone oil | 1.6 g |
| 2-Lactyl Phosphatidyl ethanol | 5.0 g |

The aqueous phase was dispersed in the oily phase at 80° C. by vigorously stirring for 5 minutes and then the mixture was cooled slowly to 25° C.

Then, this primary water/oil emulsion was dispersed in the following aqueous phase, called the external aqueous phase, by mixing gently at ambient temperature:

| | |
|---|---|
| Demineralized water SQF | 100.0 g |
| Lubragel MS (R) | 15.0 g |
| Carbopol 980 (R) | 3 g |
| Tetrasodium EDTA | 0.054 g |
| Methylparaben | 0.216 g |
| Imidazolidinyl urea | 0.216 g |
| Pure sodium hydroxide | 0.125 g |

EXAMPLE 7

Twin-phase healing emulsion

The following oily phase was heated to 80° C.:

| | |
|---|---|
| Stearyl alcohol | 1.0 g |
| Cetyl alcohol | 2.0 g |
| Cetearyl octanoate | 4.0 g |
| Polysorbate 60 | 4.0 g |
| Sorbitan stearate | 4.0 g |
| Safflower oil | 6.0 g |
| Karité butter | 3.0 g |
| Silicone oil | 0.5 g |

-continued

| | |
|---|---|
| Tocopherols | 0.05 g |
| 2-Asiaticosyl Phosphatidyl Ethanol | 0.5 g |
| 2-Madecassyl Phosphatidyl Ethanol | 0.5 g |

The following aqueous phase was heated to 80° C.:

| | |
|---|---|
| Demineralized water SQF | 100.0 g |
| Carboxyvinyl polymer | 0.3 g |
| Preservative | 0.7 g |
| Lubragel MS (R) | 5.0 g |
| Pure sodium hydroxide | 0.3 g |

The oily phase was dispersed in the aqueous phase and the mixture was stirred vigorously for 10 minutes. The emulsion thus formed was then slowly cooled to 25° C.

EXAMPLE 8

Water/silicone emulsion for the treatment of sun keratoses

The following oily phase was heated to 60° C.:

| | |
|---|---|
| Demineralized water SQF | 100.0 g |
| Sodium chloride | 0.8 g |
| Pure citric acid | 0.01 g |
| Methylparaben | 0.25 g |
| Propylene glycol | 2.0 g |
| O-cymen-5-ol | 0.1 g |

The following silicone phase was heated to 60° C.:

| | |
|---|---|
| Isocetyl stearate | 3.0 g |
| Arlacel 83 (R) | 0.8 g |
| Hydrogenated ricin oil | 0.3 g |
| Elfacos ST9 (R) | 2.0 g |
| 2-NDGA Phosphatidyl Ethanol | 2.0 g |
| DC Silicone 3225 (R) (DOW CORNING) | 9.0 g |
| Volatile silicone | 4.0 g | the aqueous phase was dispersed in the silicone phase under moderate stirring for 10 minutes and the emulsion formed was cooled to 25° C.

EXAMPLE 9

Pre-tanning emulsion with emulsifier

The following oily phase is heated to 80° C.:

| | |
|---|---|
| Wheatgerm oil | 4.0 g |
| Polyisobutene | 4.0 g |
| Octyl stearate | 4.0 g |
| Ceramide H03 | 2.0 g |
| 2-Tyrosinyl Phosphatidyl Ethanol | 2.0 g |

The following aqueous phase was heated to 80° C.:

| | |
|---|---|
| Glycerin 30' codex | 3.0 g |
| Carboxyvinyl polymer | 0.45 g |
| Lubragel MS (R) | 4.0 g |

-continued

| | |
|---|---|
| Pure sodium hydroxide | 0.055 g |
| Preservatives | 0.55 g |
| Perfume | 0.20 g |
| Demineralized water | 60.0 g |

The oily phase was dispersed in the aqueous phase with very weak stirring and high shearing for 30 minutes. Then, the emulsion formed was slowly cooled to 45° C., and the following was added under strong stirring:

| | |
|---|---|
| Talc | 3.0 g |

When the dispersion of the talc had completely finished, cooling of the mixture was continued under slow stirring. When the temperature was 25° C., the following was added under moderate agitation:

| | |
|---|---|
| Perfume | 0.2 g |

EXAMPLE 10

Anti-inflammatory emulsion an oil-in-water emulsion was prepared in the following manner.

the following oily phase was heated to 80° C.:

| | |
|---|---|
| self-emulsifying glycerol stearate (Arlacel 165 (R) from the ICI company) | 6.0 g |
| Cetyl alcohol | 1.0 g |
| Sterol of ethoxylated soya (Generol 122 E 10 (R) from the Henkel company) | 2.0 g |
| Mixture of vaseline oil and lanolin alcohol (Amerchol L101 (R) from the Amerchol company) | 3.0 g |
| Petrolatum and lanolin alcohol (Amerchol CAB (R) from the Amerchol company) | 1.0 g |
| Olive oil | 6.0 g |
| Karité butter | 3.0 g |
| Propyl paraben | 0.05 g |
| 2-glycyrrhetinyl Phosphatidyl Ethanol | 1.0 g |

The following aqueous phase was heated to 80° C.:

| | |
|---|---|
| Demineralized water | 60.0 g |
| 70% Sorbitol | 3.0 g |
| Xanthan gum | 0.3 g |
| Methylparaben | 0.1 g |

When the Xanthan gum was well dispersed, the oily phase was added to the aqueous phase at 80° C., and vigorous stirring was carried out for 20 minutes to form the emulsion. Then, the stirring was reduced and the emulsion was slowly cooled to 40° C. Then, 2 g of water containing 0.15 g of imidazolidinyl urea and then 0.3 g of perfume were added to it.

Test of the Activity of an Active Phospholipid

As an example, the comedolytic power of all-trans 2-retinoyl phosphatidinyl ethanol was tested following the protocol below:

The animal chosen for the test of comedolytic activity was the Hairless rhino (hr rh) mouse of female sex, this choice being due to the fact that the skin of such an animal has a high density of comedones having a large diameter and narrow orifice. The use of comedolytic agents on the skin of the animal provokes the opening of the orifice of the comedones, the release of the horny material and the sebum that it contains.

Two groups comprising six mice each which were six-week's old at the start of the test and weighing on average 18 grams each were used. The first group were mice treated with distilled water (negative control group) and the second group were mice treated with the product under study. The treatment consisted of a topical use of the product studied on the interscapular area at a dose of 0.02 ml, 5 days out of 7, for 21 days. The animals were sacrificed at the end of three weeks of treatment, 24 hours after the last application.

Biopsies of the skin were then taken from the treated areas of the animals and from these biopsies, sections were prepared for a standard morphometric study by methods known to a man skilled in the art. The following parameters were measured: diameter of the opening of the comedon at the surface i.e d

| | |
|---|---|
| diameter of the comedon | i.e D |
| comedonian profile | i.e R = d/D |

The ratio R=d/D allowed the action of the comedolytic agents to be quantified.

The percentage of inhibition of the comedones was calculated for the product under study relative to the negative control, i.e. The following ratio:

$$\% \text{ inhibition} = \frac{(\text{product } R - \text{negative control } R) \times 100}{\text{negative control } R}$$

The comedolytic activity of all-trans 2-retinoyl phosphatidinyl ethanol at 0.1% in solution in ethylenediglycol was measured by this method and produced the following results:

| | |
|---|---|
| Product R = | 0.89 |
| Negative control R = | 0.78 |
| % inhibition = | 14.1% |

Therefore it can be seen that all-trans 2-retinoyl phosphatidinyl ethanol at a dose of 0.1% had a good comedolytic activity.

Various modifications of the compositions and method of the invention may be made without departing from the spirit or scope thereof and it is to be understood that the invention is intended to be limited only as defined in the appended claims.

What is claimed is:

1. A phospholipid of formula I:

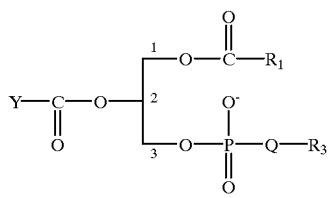
(I)

wherein:
$R_1$ is an aliphatic chain having 14 to 24 carbon atoms which is saturated or has 1 or 2 unsaturations,
$R_3$ is ethyl, propyl or butyl and
Y—CO— is a group derived from an acid selected from the group consisting of vitamin A acid, all-trans retinoic acid, 9-cis retinoic acid, 13-cis retinoic acid, gamma-linolenic acid, alpha-linolenic acid, eicosapentaenoic acid (EPA), docosahexaenoic acid (DHA), glycolic acid, lactic acid, tartaric acid, alpha-methyllactic acid, alpha-hydroxybutyric acid, gluconic acid, mandelic acid, mucic acid, malic acid, alpha phenyllactic acid, saccharic acid, tartronic acid, kojic acid, asiatic acid, madecassic acid, benzoic acid, glutamic acid, malonic acid, phytic acid, ascorbic acid, nordihydro guaiaretic acid, salicylic acid, 18β-glycyrrhetinic acid, tyrosine, hydroxyproline, lysine, arginine, pyroGlu-Glu-Asp-Ser-GlyOH, Gly-His-Lys, Arg-Gly-Asp-Ser, farnesil succinate retinol succinate and a diacid derivative of the formula

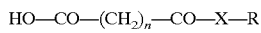
HO—CO—(CH$_2$)$_n$—CO—X—R wherein n is 2–16, X is a sulphur, nitrogen or oxygen atom and R is a group of formula Y—CO— as defined above.

2. A phospholipid as claimed in claim 1, wherein the chain $R_1$ is a palmitic, oleic, linoleic, stearic or myristic chain.

3. A phospholipid as claimed in claim 1, wherein the group Y—CO— is derived from an acid selected from the group consisting of vitamin A acid, linolenic acid, eicosapentaenoic acid (EPA), docosahexaenoic acid (DHA), kojic acid, asiatic acid, madecassic acid, glutamic acid, phytic acid, ascorbic acid, lactic acid, glycolic acid, nordihydroguaiaretic acid, tyrosine, pyroGlu-Glu-Asp-Ser-GlyOH, Gly-His-lys,Arg-Gly-Asp-Ser and 18β-glycyrrhetinic acid.

4. A phospholipid as claimed in claim 1, wherein $R_3$ is ethyl.

5. A phospholipid as claimed in claim 1, wherein the group Y—CO— is derived from vitamin A acid, all-trans retinoic acid, 9-cis retinoic acid or 13-cis retinoic acid and $R_3$ is ethyl.

6. A process for preparing a phospholipid of formula I as defined in claim 1, comprising subjecting a phospholipid of formula II

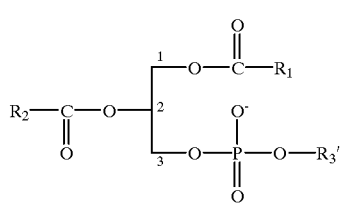
(II)

wherein $R_1$ and $R_2$, identical or different, are an aliphatic chain having 14 to 24 carbon atoms which is saturated or has 1 or 2 unsaturations and $OR_3'$ is a group derived from choline, ethanolamine, glycerol, serine or inositol, to an enzymatic transphosphatidylation to obtain a product of formula (III)

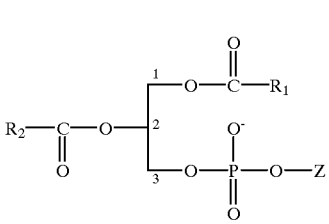
(III)

wherein $R_1$ and $R_2$ have the meanings indicated above and Z is an ethyl, propyl or butyl radical, subjecting the product of formula (III) to an enzymatic hydrolysis of the ester function in position 2 of the glycerol, in order to obtain a product of formula (IV)

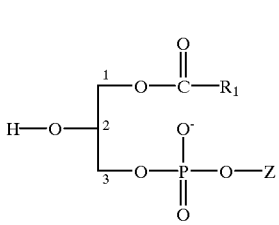
(IV)

wherein $R_1$ and Z have the meanings indicated above, and subjecting the product of formula (IV) to an acylation reaction of the hydroxyl, by an anhydride of formula (V)

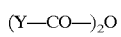
(Y—CO—)$_2$O (V)

wherein Y—CO— is a group as defined in claim 1.

7. The process as claimed in claim 6, wherein the phospholipid is phosphatidylcholine or phosphatidylethanolamine.

8. The process as claimed in claim 6, wherein the substitution of the group $R_3'$ or the group Z which is carried out by enzymatic transphosphatidylation is achieved by means of phospholipase D in an ethanolic, propanoic or butanoic medium.

9. The process as claimed in claim 6, wherein the enzymatic hydrolysis to obtain the product of formula (IV) is achieved by means of phospholipase A2, which enzyme is used in a non-purified form, in a $Ca^{2+}$ medium.

10. The process as claimed in claim 6, wherein the acylation of the hydroxyl in the compound of formula (IV) is carried out by an enzymatic or chemical route, after acidification of the compound of formula (IV), using a single or mixed anhydride active substance, in a solvent of ether or toluene.

* * * * *